United States Patent [19]

Marquis et al.

[11] 4,036,880

[45] July 19, 1977

[54] METHOD OF PREPARING POLYAMINOPOLYPHENYLMETHANES

[75] Inventors: Edward T. Marquis; Robert M. Gipson; Lewis W. Watts, Jr., all of Austin, Tex.

[73] Assignee: Texaco Development Corporation, New York, N.Y.

[21] Appl. No.: 723,422

[22] Filed: Sept. 15, 1976

[51] Int. Cl.$^2$ .............................................. C07C 85/24
[52] U.S. Cl. ................................................ 260/570 D
[58] Field of Search .................................... 260/570 D

[56] References Cited

U.S. PATENT DOCUMENTS 3,362,979  1/1968  Bentley .............................. 260/570 X

*Primary Examiner*—Robert V. Hines
*Attorney, Agent, or Firm*—Carl G. Ries; Thomas H. Whaley; James L. Bailey

[57] ABSTRACT

Covers a method of preparing diaminodiphenylmethanes and higher homologues thereof which comprises the step of condensing aniline and formaldehyde in the presence of a molybdenum boride catalyst.

4 Claims, No Drawings

METHOD OF PREPARING POLYAMINOPOLYPHENYLMETHANES

BACKGROUND OF THE INVENTION

1. Field of the Invention

This invention relates to the field of polyamines.

2. Description of the Prior Art

The process of producing aromatic polyamines by the reaction of aniline and formaldehyde is well known and described for example in U.S. Pat. Nos. 2,683,730; 3,277,173; 3,344,162; and 3,362,979. By phosgenating these amines the corresponding isocyanates are obtained.

The polyamines produced by the condensation of aniline and formaldehyde usually consists of a mixture of poly(methylenephenylamines) of functionality greater than two and the 2,2', 2,4' and 4,4' isomers of diaminodiphenylmethane. By reaction with phosgene a corresponding mixture of polyisocyanates and diisocyanates is prepared which is useful in producing, for example, polyurethane foam.

One mode of reacting aniline with formaldehyde is to effect this reaction in the presence of a strong mineral acid, such as hydrochloric acid. Here a reaction occurs between the corresponding aniline hydrochloride and formaldehyde to provide a reaction mixture which, upon neutralization with a base, may be treated to recover the polyphenylamines. This process has left much to be desired. For example, it is necessary to utilize large quantities of both a mineral acid and a base which adversely affect the economics of the process and also the ease of conducting the reaction. In addition, the use of large quantities of mineral acids and bases presents a severe corrosion problem. Also, the inorganic salt formed poses environmental difficulties with respect to disposal and/or recovery.

As an improvement to the conventional mineral acid catalyzed aniline-formaldehyde condensation use of a solid acidic siliceous catalyst has been proposed (See U.S. Pat. No. 3,362,979). This is economically favorable over the conventional hydrochloric acid catalyzed process since use of large quantities of corrosive acid and caustic are avoided. However, even this process has some drawbacks, particularly, in that the rate of reaction is not as rapid as desired and rearrangement of product amines at conventional conditions is not considered sufficiently complete.

SUMMARY OF THE INVENTION

The invention relates to a process for making aromatic polyamines by the reaction of aniline and formaldehyde in the presence of a molybdenum boride catalyst.

DESCRIPTION OF THE PREFERRED EMBODIMENTS

A method of preparing diaminodiphenylmethane and higher homologues thereof has now been discovered. The invention comprises the step of condensing aniline and formaldehyde in the presence of a molybdenum boride catalyst. A mixture of products is produced which includes the diaminodiphenylmethane isomers comprising the 2,2', 2,4' and 4,4' diamine isomers and higher homologues thereof or polymethylene polyphenylamines. The latter are higher molecular weight condensation polymers of the formaldehyde and the aniline and are considered homologues of the simple diaminodiphenylmethane isomers.

Depending upon reaction conditions, amount of catalyst employed, proportions of the reactants, and other variables the proportions of diamines, and higher polyamines present in the final reaction mixture may be widely varied. However, usually, the reaction mixture contains 20–80% by weight of diamine with the remainder being higher polyamines thereof. More often the percentage of diamines in the mixture is 30–70% and most often ranges from about 35 to about 55 weight percent. Correspondingly the polymeric products higher than the dimer products usually in the preferred embodiment range from the 30 to 70% by weight, and most often range from about 45 to about 65% by weight. With respect to product distribution of the dimer usually 1–10% by weight of total dimer is the 2,2' isomer, with the remainder being 2,4' and 4,4' isomers. Most often the content of dimer is 1–5% 2,2' isomer with the remainder, or 95–99% being 2,4' and 4,4' isomers, based on total dimer content. Generally the higher molecular weight polymethylene polyphenylpolyamines have an average functionality of from about 2.1 to about 3.0, more often 2.2–2.7.

The molybdenum boride catalyst may be chosen from a wide variety of molecular forms. Preferred catalyst of this type include molybdenum boride (MoB), molybdenum diboride (MoB$_2$), dimolybdenum monoboride (Mo$_2$B) and dimolybdenum pentaboride (Mo$_2$B$_5$). The amount of catalyst used may be varied according to the choice of the experimenter. Usually, however, 0.5–3.0% by weight of catalyst based on weight of aniline is employed. More often the amount of catalyst utilized is 1–2% by weight based on aniline weight.

In order to prepare the methylene-bridged polyphenyl polyamines (term includes both diaminodiphenylmethane isomers and higher homologues thereof or higher polymers) the following process conditions are preferred.

The molar ratio of aniline to formaldehyde may be varied within comparatively wide limits. Thus, for example, from about one to about ten mols of aniline may be employed per mol of formaldehyde. In general, at the lower aniline: HCHO ratios, such as ratios of from about 1:1 to about 2.5:1, the higher polymers will be formed preferentially and the yield of higher polymers is in excess of the yield of dimer. However, as progressively larger amounts of aniline are used, the yield of dimer is progressively increased at the expense of polymer yield. Thus, with aniline to formaldehyde ratios of from about 3:1 to about 10:1 or more, the reaction product will be composed primarily of the dimer. As indicated above, the dimer will be formed as a mixture of the 2,4'- and 4,4'-diamine isomers.

Formaldehyde may be employed in any of its commercially available forms. Thus, formalin, paraformaldehyde, "stabilized" methanol solutions of formaldehyde, etc., may be employed.

The reaction may be conducted in the presence or absence of a solvent. When a solvent is to be employed, it may be any of the conventionally known hydrocarbon solvents or chlorinated hydrocarbons, such as aromatic or aliphatic solvent boiling within the range from about 100° to about 200° C. The solvent should be employed in an amount sufficient to provide a single phase solution of the amine compound.

The reaction conditions to be employed may suitably include a reaction temperature within the range of about 100° to about 300° C., and more preferably within the range of about 150° to about 250° C.

Pressure is not particularly critical with respect to the process. However, the pressure should be sufficient to provide for liquid phase reaction conditions. Thus, pressures ranging from atmospheric up to 1000 psig may be employed.

The reaction proceeds smoothly under the above-described conditions, and is normally substantially complete upon addition of the formaldehyde. However, because of the exothermic nature of the reaction, it is normally preferable to add the formaldehyde at a rate such that the desired reaction temperature can be maintained. It is normally possible to bring the reaction to completion within from about five minutes to about eight hours in conventional equipment. More often the reaction is complete in 1¾–4 hours.

The polyaminopolyphenylmethanes of the present invention are recovered from the reaction mixture by any desired means. They are conveniently recovered by filtering the catalyst and removing water and excess aniline under reduced pressure. The bottoms from these operations will consist of diamine and polyamine in proportions depending on the ratio of aniline to formaldehyde, as indicated above. If it is desired to separate the diamine from the polyamine, this is easily accomplished by simple distillation whereby the diamine is flashed from the non-volatile polyamine residue. The overhead product may be removed, for example, at from about 170° to about 200° C, at about 0.5 to about 0.025 mm. Hg pressure and will consist essentially of diaminodiphenylmethane.

The dimer and higher products of the present invention are useful for a variety of purposes. For example, they may be utilized as raw materials for the production of the corresponding polyisocyanates, or used as such as epoxy curing agents.

The advantages in using a boride catalyst in the process of the invention are many and varied. In the first place a completely rearranged product is achieved in a desirable manner. In addition, many commonly used catalysts such as hydrochloric acid are highly corrosive whereby there is no indication here that the molybdenum borides are corrosive in any manner. Again, it has been found, as will be seen in more detail hereinafter, that the borides of molybdenum are considerably more active than other known catalysts such as silica-alumina, which latter catalyst does, however, avoid the discussed problems of corrosion. Again, only small amounts of catalyst need be employed and the catalyst is readily removed from the reaction mixture by filtration. Surprisingly, complete rearrangement of product amine occurs at conditions which, with silica-alumina catalyst, do not afford a suitable product. Lastly, very little molybdenum metal is found soluble in the product amine when molybdenum borides are used as catalysts, whereas, when other molybdenum compounds are used, the soluble molybdenum content in the product is much higher.

The following examples illustrate the process of the invention. It is understood, of course, that these examples are merely illustrative, and that the invention is not to be limited thereto.

EXAMPLE I

Aniline (186.0 g, 2.0 moles), formalin (75 ml or 1.0 mole formaldehyde), and catalyst, molybdenum diboride (1.9 g or 1.0% by wt basis aniline charged) were added to a stirred 1 l. autoclave and flushed with $N_2$. The reactants and catalyst were heated to 200° C under autogenous pressure and held there for a 1 hour holding period. The reaction mixture was cooled, and poured up from the autoclave. Work-up was as follows: The water was removed using a rotary evaporator and aspirator vacuum and a hot water bath operation at 80°–90° C. After water removal the catalyst was removed by filtration and the aniline stripped to afford an amine product with the following properties: total titratable amine = 9.55 meq/g, molecular weight of 287 (Mn): the NMR spectrum indicated only 4.1% N-benzyl secondary amine content and 5.5% N-methyl secondary amine content. The GLC indicated 44.7 weight percent MDA (methylenedianilines) with an isomer distribution as follows: unknowns = 1.9%, 2,2'-MDA = 2.4%, 2,4'-MDA = 25.2%, 4,4'-MDA = 65.0% and N-methyl = 5.5%. Atomic absorption found only 24 ppm. molybdenum in the product amine.

EXAMPLE II

In a run exactly as described in Example I except that the catalyst was molybdenum boride, a product amine was obtained with 9.51 meq/g total titratable amine content. The NMR spectrum indicated complete rearrangement of the secondary (N-benzyl) amine and the GLC indicated a 41.7% MDA content with the MDA portion having the following isomer distribution: unknowns = 0.4%, 2,2'-MDA = 2.0%, 2,4'-MDA = 28.0%, 4,4'-MDA = 66.9% and N-methyl = 2.7%. Atomic absorption indicated only 26 ppm molybdenum in the amine product.

EXAMPLE III

Again, in a run like Example I except that the catalyst was dimolybdenyum monoboride, an amine product was obtained with 9.38 meq/g total titratable amine content. The NMR spectrum indicated 6.3% N-benzyl type secondary amine. The GLC indicated some 42.7% MDA with an isomer distribution as follows: unknowns = 1.7%, 2,2'-MDA = 1.6%, 2,4'-MDA = 27.4%, 4,4'-MDA = 66.7%, and N-methyl = 2.6%. Atomic absorption indicated the presence of about 171 ppm. molybdenum in the product amine.

EXAMPLE IV

Similarly to Example I, except that the catalyst was dimolybdenum pentaboride, an amine product was obtained with 9.37 meq/g total titratable amine content. The NMR spectrum revealed some 8.0% N-benzyl secondary amine and 3.4% aminal or related secondary amine. The GLC indicated the MDA was 44.7 weight percent and the isomer distribution in the MDA portion showed 64.3% 4,4'-MDA content. The amine product contained 130 ppm. molybdenum by atomic absorption spectroscopy.

EXAMPLE V

Here a control run was made using no catalyst. To a 1 l. stirred autoclave were added aniline (372.0 g, 4.0 moles), and formalin (60.0 g. formaldehyde, 2.0 moles). The autoclave was flushed with $N_2$ and heated to 200° C and held there for 1 hour. Work-up as described in Example I afforded a crude amine with an NMR spectrum indicating 32.8% secondary (N-benzyl) amine and 22.9% secondary amine likely of the aminal type. Further the N-methyl secondary amine was 14.5% (double the normal values obtained in catalyzed processes). This product represents a grossly incomplete reaction process in which the majority of the material is in an unrearranged state.

EXAMPLE VI

Here a control run was made using a silica-alumina catalyst. In an example run exactly like Example V except that 3.7 g silica alumina catalyst (1.0% of the aniline charged) was added to the autoclave in addition to the reactants, a product amine was obtained with 9.43 meq/g total titratable amine content. The NMR spectrum indicated the presence of some 12.1% unrearranged secondary amine of the N-benzyl type and 6.1% N-methyl secondary amine. The GLC indicated 47.5% MDA with 61.6% 4,4'-MDA present in the dimer portion.

We claim:

1. A method of preparing diaminodiphenylmethane and higher homologues thereof which comprises the step of condensing aniline and formaldehyde in the presence of a molybdenum boride catalyst.

2. The method of claim 1 wherein said catalyst is present in an amount ranging from about 0.5 to about 3.0% by weight based on the weight of aniline present.

3. The method of claim 2 wherein said catalyst is present in an amount of 1-2% by weight.

4. The method of claim 1 wherein said catalyst is selected from the group consisting of molybdenum boride, molybdenum diboride, dimolybdenum monoboride, and dimolybdenum pentaboride.

* * * * *